US00RE36062E

United States Patent [19]

Speelman et al.

[11] E Patent Number: Re. 36,062

[45] Reissued Date of Patent: Jan. 26, 1999

[54] STEAM STERILIZATION INDICATOR

[75] Inventors: Irving A. Speelman, Fort Meyers, Fla.; Frank E. Platko, Shelton, Conn.; Kenneth A. Summer, Columbia, S.C.; Seymour Schuman, New York, N.Y.

[73] Assignee: Propper Manufacturing Co., Inc., Long Island City, N.Y.

[21] Appl. No.: 325,607

[22] Filed: Oct. 19, 1994

Related U.S. Patent Documents

Reissue of:

[64] Patent No.: 5,158,363
Issued: Oct. 27, 1992
Appl. No.: 746,442
Filed: Aug. 16, 1991

[51] Int. Cl.[6] ..... G01K 3/04; G01K 11/12

[52] U.S. Cl. ..... 374/102; 374/106; 116/207; 116/219

[58] Field of Search ..... 116/206, 207, 116/217, 219, 280; 374/102, 104, 106, 160, 162; 422/58

[56] References Cited

U.S. PATENT DOCUMENTS

| | | | |
|---|---|---|---|
| 2,118,144 | 5/1938 | Berman et al. | 374/162 |
| 2,335,999 | 12/1943 | Diack | 374/160 X |
| 2,826,073 | 3/1958 | Huyck et al. | 374/102 |
| 3,114,349 | 12/1963 | Schuman | 116/201 |
| 3,360,337 | 12/1967 | Edenbaum et al. | 116/207 X |
| 3,360,338 | 12/1967 | Edenbaum et al. | 116/207 X |
| 3,360,339 | 12/1967 | Edenbaum et al. | 116/207 X |
| 3,414,415 | 12/1968 | Broad, Jr. | 116/219 |
| 3,479,877 | 11/1969 | Allen et al. | 374/106 |
| 3,981,683 | 9/1976 | Larsson et al. | 374/106 X |
| 3,996,802 | 12/1976 | Smith | 116/207 X |
| 4,121,714 | 10/1978 | Daly et al. | 116/207 X |
| 4,179,397 | 12/1979 | Rohowetz et al. | 116/207 X |
| 4,298,569 | 11/1981 | Read | 422/27 |
| 4,410,493 | 10/1983 | Joslyn | 422/58 |
| 4,448,548 | 5/1984 | Foley | 374/160 |
| 4,692,307 | 9/1987 | Bruso | 422/58 |
| 5,066,464 | 11/1991 | Augurt | 422/58 |

FOREIGN PATENT DOCUMENTS

| | | |
|---|---|---|
| 1215891 | 12/1970 | United Kingdom . |
| 91/09287 | 6/1991 | WIPO . |

*Primary Examiner*—William A. Cuchlinski, Jr.
*Assistant Examiner*—Willie Morris Worth
*Attorney, Agent, or Firm*—Oppedahl & Larson

[57] ABSTRACT

A steam sterilization indicator for indicating both exposure to steam and sterilization is provided. The steam sterilization indicator includes a backing member. A tablet formed of a compound having a first melting point and second melting point which is lower that the first melting point, the second melting point being the melting point of the compound exposed to steam is also provided. A wick is affixed to the backing member adjacent to the tablet. A steam permeable material covers the tablet and the wick. Upon melting, the tablet material is absorbed by the wick. A handle is affixed to the backing member. One end of the handle includes a steam exposure indicator formed of a color changing ink which changes color in the presence of steam.

4 Claims, 2 Drawing Sheets

10
12
14
16
18
20
22
24
26
28
30
32
34
REJECT
ACCEPT

REJECT
ACCEPT
10
12
14
16
18
20
22
24
26
30
32
36
6
7
8

STEAM STERILIZATION INDICATOR

Matter enclosed in heavy brackets [ ] appears in the original patent but forms no part of this reissue specification; matter printed in italics indicates the additions made by reissue.

BACKGROUND OF THE INVENTION

The present invention is directed to a steam sterilization indicator, and more particularly, to an indicator for monitoring the extent of exposure of a device to steam as well as whether or not exposure to steam has occurred.

Steam sterilization indicators are well known in the art as exemplified by U.S. Pat. Nos. 3,981,683 and 4,448,548. These indicators generally include a backing strip of a dimensionally stable material such as aluminum foil or the like. A fusible material usually formed in tablet form is deposited on the backing strip. A wick is attached to the backing strip with one end of the wick in intimate contact with the fusible tablet. A transparent plastic covers the tablet and the wick and is adhered to the backing strip. The normal melting point of the fusible tablet is depressed in the presence of saturated steam and upon exposure to saturated steam over a predescribed time period melts. The tablet melt is absorbed by the wick producing a visual indication of the device's integration of the exposure time and temperature in the presence of saturated steam.

However, such steam sterilization indicators are often utilized deep within fabric packs incorporating towels or the like. Accordingly, these pack/indicator combinations frequently suffer from the disadvantage that in order to determine whether the pack has actually been exposed to steam during a sterilization cycle, the pack must be unravelled. (destroying the integrity of the pack) to determine whether the fusible material has melted at all possibly indicating that exposure to a sterilizing amount of steam has occurred. If there is no indication of exposure to steam, then the pack must be repackaged resulting in inefficiencies requiring the waste of time of test personnel. Additionally, the prior art device lends itself to false readings. If in fact the device was exposed to steam, and the device was not exposed to steam of a high enough temperature or for a long enough period to melt the fusible material, when the pack is unwrapped, it will appear as if the pack has never been exposed to steam, providing a false reading.

Accordingly, a steam sterilization indicator which indicates exposure to steam without the necessity of unwrapping the pack is desired with attendant marked advantages.

SUMMARY OF THE INVENTION

Generally speaking, in accordance with the present invention, a steam sterilization indicator includes a backing strip of a dimensionally stable material. A fusible material is deposited on the backing strip, the material having a normal melting point which is lower in the presence of saturated steam. The wick is mounted on the backing strip having one end in intimate contact with the fusible material. A steam permeable transparent plastic material is mounted over the wick and affixed to the backing strip. A handle is coupled to the backing strip and has provided thereon at an end opposite the end affixed to the backing strip a steam exposure indicator.

Accordingly, it is an object of the invention to provide an improved steam sterilization indicator.

Another object of the invention is to provide a steam sterilization indicator which indicates exposure of the indicator to steam without destruction or unwrapping of the fabric pack.

Yet another object of the invention is to provide a steam sterilization indicator which allows removal of the steam sterilization indicator from the fabric pack without destruction of the pack.

A further object of the invention is to provide a more efficient steam sterilization indicator.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

Reference is had to the following description, taken in connection with the accompanying drawings, in which.

DETAILED DESCRIPTION OF THE PREFERRED EMBODIMENT

Figures 1, 2:
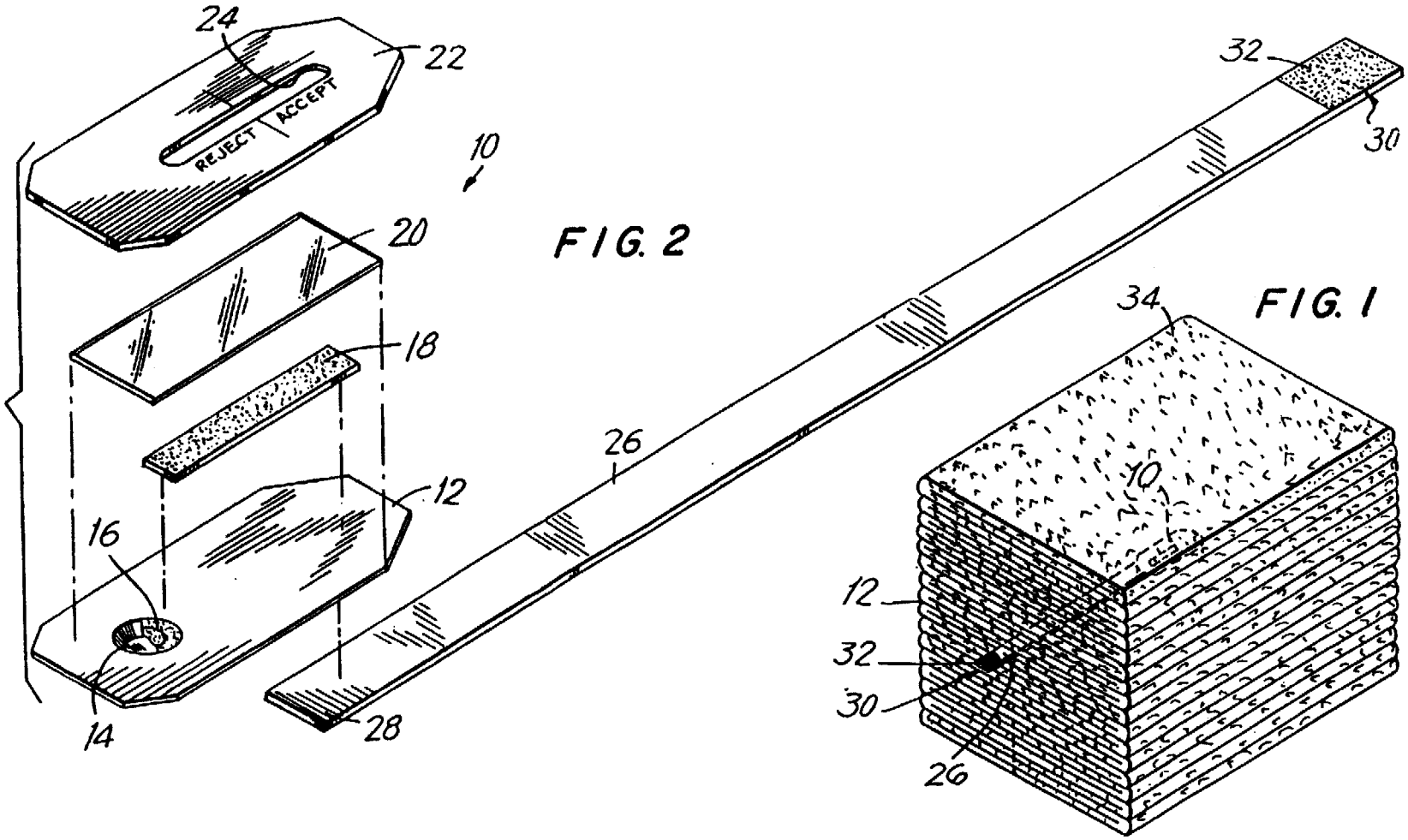
FIG. 1 is a perspective view of a steam sterilization indicator constructed in accordance with the invention shown in phantom in use with a test pack.
FIG. 2 is an exploded view of a steam sterilization indicator constructed in accordance with the invention.

Reference is made to FIGS. 2 and 6–8 wherein a steam sterilization indicator, generally indicated as 10, constructed in accordance with the invention is provided. Steam sterilization indicator 10 includes a backing member 12. Backing member 12 is formed of a material which is dimensionally stable when exposed to sterilizing steam, such as aluminum foil or the like. Backing member 12 is formed with a cup-like depression 14 for receiving a tablet 16 of fusible material. Tablet 16 is a material such as an organic compound mixed with a dye or the like. The material of tablet 16 melts or fuses at a predetermined temperature and above. However, the normal melt temperature is lowered in the presence of saturated steam. A wick 18 absorbent to the molten material of tablet 16 is mounted on backing member 12 in intimate contact with tablet 16. In the present embodiment tablet 16 includes a dye to facilitate observation of the movement of the molten material along wick 18.

Tablet 16 is formed of an organic compound which is water soluble and whose normal melting or fusing point in the absence of steam is greater than the sterilization temperature to be monitored. Accordingly, the device is inoperative in the absence of water vapor at the sterilization temperature. By way of example, the compound formed in tablet 16 should contain the functional groups which would result in a degree of water solubility. Illustrative of these functional groups are aldehyde, carbonyl, ester, keto, ether, hydroxy, amino, amide, carboxy, phosphate, phosphonate sulfones, sulfate, sulfonate or the like. The compounds further are heterogeneous compounds which contain carbon and oxygen or nitrogen in the structure. In addition to oxygen and nitrogen, other non-reactive substituents may be included such as chlorine, sulfur, phosphorous or the like.

A cover strip 20 is adhesively mounted to backing member 12. Wick 18 and tablet 16 are disposed between cover strip 20 and backing member 12. Backing member 12 acts as a substrate supporting tablet 16, wick 18 and cover strip 20. Cover strip 20 is formed of a steam permeable material of a predetermined vapor transmission rate. The thickness of the cover strip 20 as well as the material used controls the rate at which tablet 16 melts. Cover strip 20 controls exposure of the moisture sensitive compound of tablet 16 to the saturated steam as cover strip 20 is slowly permeable to moisture transmission. In an exemplary embodiment, cover strip 20 is formed of a transparent polymeric composition such as polypropylene, polyethylene, polystyrene or the like.

An indicating cover 22 is affixed to cover strip 20 by an adhesive or the like and overlies cover strip 20. Indicating cover 22 is formed with a cut-out window 24 therein. Window 24 overlies wick 18 and, since cover strip 20 is transparent, allows wick 18 to be viewed through indicating cover 22.

A handle 26 is affixed to backing member 12 at a first end 28. A steam sensitive ink 32 is provided at second opposed end 30 of handle 26. Steam sensitive ink 32 changes color when exposed to steam over a predetermined time period less than the time period required for tablet 16 to melt and travel along wick 18. In an exemplary embodiment, ink 32 changes from a substantially off-white to yellow tint to dark brown or black when exposed to steam for between 30 seconds to 45 seconds. The length of handle 26 is sufficient to extend externally of a towel or linen sterilization pack 34 while backing member 12 is buried within the towel or linen pack.

Reference is now made to FIGS. 1 and 3–5 wherein the operation of steam sterilization indicator 10 in accordance with the invention is provided. A steam sterilization test pack 34 is formed of a folded towel or linen cloth. A steam sterilization indicator 10 is buried well within test pack 34 to simulate a sterilization condition so that steam reaching the portion of steam sterilization indicator 10 which includes tablet 16 must sufficiently penetrate test pack 34. A portion of handle 26 including end 30 and indicating dye 32 extends externally of test pack 34.

Figures 3, 4, 5, 6, 7, 8:
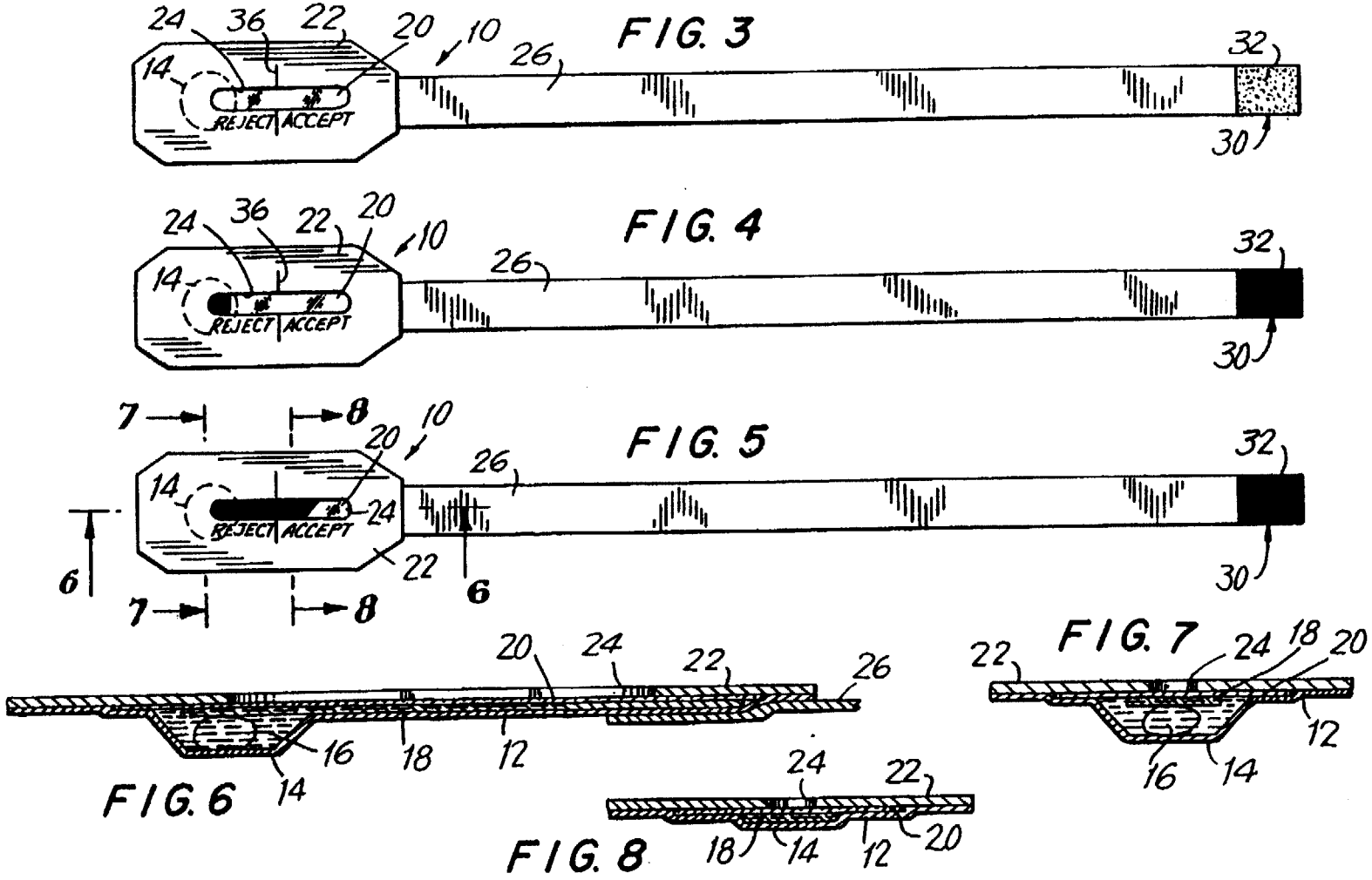
FIG. 3 is a top plan view of a steam sterilization indicator constructed in accordance with the invention prior to exposure to steam.
FIG. 4 is a top plan view of a steam sterilization indicator constructed in accordance with the invention after exposure to steam for a time period less than necessary for sterilization.
FIG. 5 is a top plan view of a steam sterilization indicator constructed in accordance with the invention after exposure to an amount of steam necessary for steam sterilization.
FIG. 6 is a sectional view taken along lines 6—6 of FIG. 5.
FIG. 7 is a sectional view taken along lines 7—7 of FIG. 5.
FIG. 8 is a sectional view taken along lines 8—8 of FIG. 5.

Prior to exposure to steam, steam sterilization indicator 10 is in a clear state, as shown in FIG. 3. In a clear state, steam indicating ink 32 has not changed color and tablet 16 has not melted. Accordingly, a technician looking at test pack 34 with the steam sterilization indicator 10 of FIG. 3 embedded therein would easily observe that the test pack has not undergone steam sterilization or has been exposed to steam for an insignificant amount of time. This determination would be made without opening or destroying the test pack. Test pack 34 is then placed in the presence of steam. As steam sterilization indicator 10 is exposed to steam, ink 32 changes to a second color such as dark brown or black, as shown in FIG. 4. Additionally, steam penetrates cover strip 20 lowering the melting point of tablet 16, causing tablet 16 to melt. As tablet 16 melts, it is absorbed by wick 18 and begins to travel along wick 18 towards handle 26. A technician viewing the test pack 34 would observe that test pack 34 had been exposed to saturated steam for at least 30 to 45 seconds, a substantial amount of time. Indicating cover 22 is provided with a marking line 36, if the flow of the melted tablet 16 travels across indicating line 36 as seen in FIG. 5, then test pack 34 has been exposed to saturated steam for a sterilizing period. Accordingly, the materials being sterilized along with test pack 34 would be "accepted" as indicated on indicating cover 22 for further use. If the flow of melted material of tablet 16 has not crossed line 36, then test pack 34 has not been exposed to a sufficient amount of saturated steam and therefore the materials should be rejected as indicated on indicating panel 22. The technician, seeing that the test pack 34 had in fact been exposed to saturated steam by the change in color of indicating ink 32 would remove steam sterilization indicator 10 by handle 26, sliding steam sterilization indicator 10 from test pack 34 without destroying test pack 34. If, upon investigating steam sterilization indicator 10, the steam sterilization indicator 10 resembles that of FIG. 4, the test pack would be rejected. If it resembles the steam sterilization indicator of FIG. 5, the material sterilized with sterilization test pack 34 would be accepted.

By providing a handle with a steam sterilization indicator, it becomes possible to observe the results of steam sterilization techniques without opening the test pack in which the steam sterilization indicator is embedded. Additionally, by providing a steam exposure indicating ink at a far end of the handle, extending without a fabric (towel or linen) pack, it becomes possible to determine whether or not a steam sterilization indicator and pack have been exposed to steam without destroying the pack and without requiring double processing of the pack if in fact the steam sterilization indicator has not been exposed to steam. Accordingly, the structure defined above combines a sterilization indicator with a steam exposure indicator in a single construction.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A steam sterilization indicator for [use in] *monitoring sterilization of* a fabric pack *at a predetermined sterilization temperature* comprising:

(*a*) *an internal sterilization indicator to be disposed within the fabric pack comprising* a backing strip;

a tablet formed of a compound having a normal melting point greater than [a] *the* predetermined *sterilization* temperature, said melting point being depressed below said predetermined *sterilization* temperature by absorption of water into the compound when said compound is exposed to saturated steam at the predetermined *sterilization* temperature, [said predetermined temperature being below the normal melting point of the compound,] said tablet being mounted on said backing strip;

wicking means for absorbing the compound after melting of the tablet disposed on said backing strip, said wicking means having a first end positioned in intimate contact with said compound;

a transparent steam permeable membrane adhesively bonded to said backing strip and covering said tablet and said wicking means, said steam permeable membrane controlling the exposure of said tablet to steam; *and*

*acceptance indicating means for determining, in cooperation with said wicking means and absorbed compound whether the internal sterilization indicator has been exposed to conditions of steam and temperature for a period of time sufficient to achieve sterilizing conditions within the fabric pack;*

(*b*) a handle having a first end [and second end] affixed to said backing strip at said first end *of said internal sterilization indicator*, said handle being dimensioned to extend externally of said fabric pack when said [backing strip] *internal sterilization indicator* is disposed within said fabric pack*;* and (*c*) *a* steam exposure [indicating means] *indicator* mounted on said handle at [said] *a* second end*, remote from said first end,* for indicating exposure of said steam sterilization indicator to steam [and acceptance indicating means for determining, in cooperation with said wicking means and absorbed compound, whether said fabric pack has been sterilized]*, wherein said steam exposure indicator provides a positive indication of exposure to steam in less time than is required for the internal sterilization indicator to provide a positive response at the predetermined sterilization temperature*

.

2. The steam sterilization indicator of claim 1, wherein said acceptance indicating means includes an indicating cover disposed over said steam permeable membrane having a window formed therein for allowing observation of said absorbed compound as said absorbed compound travels along said wicking means and further including an indicator for indicating whether said tablet has melted sufficiently to indicate sterilization of said fabric pack.

3. The steam sterilization indicator of claim 1, wherein said steam exposure indicating means includes a steam sensitive ink, said steam sensitive ink changing color upon exposure to said saturated steam for a predetermined temperature and time interval, said ink being disposed on said handle, a portion of said handle including said ink extending without said fabric pack.

4. A steam sterilization indicator for use in a fabric pack comprising:

a backing strip:

a tablet formed of a compound having a normal melting point greater than a predetermined temperature, said normal melting point being depressed below said predetermined temperature by absorption of water into the compound when said compound is exposed to saturated steam at the predetermined temperature, said predetermined temperature being below the normal melting point of the compound, said tablet being mounted on said backing strip;

wicking means for absorbing the compound after melting of the tablet disposed on said backing strip, said wicking means having a first end positioned in intimate contact with said compound;

a transparent steam permeable membrane adhesively bonded to said backing strip and covering said tablet and said wicking means, said steam permeable membrane controlling the exposure of said tablet to steam;

a handle affixed to said backing strip, said handle being dimensioned to extend without said fabric pack when said backing strip is disposed within said fabric pack;

steam exposure means for indicating exposure of said steam sterilization indicator to saturated steam for a predetermined temperature and time period;

said steam exposure indicating means including a steam sensitive ink, said steam sensitive ink changing color upon exposure to said saturated steam for a predetermined temperature and time interval, said ink being disposed on said handle, a portion of said handle including said ink extending without said fabric pack; and acceptance indicating means for determining in cooperation with said wicking means and absorbed compound, whether said fabric pack has been sterilized, said acceptance indicating means including an indicating cover disposed over said steam permeable membrane having a window formed therein for allowing observation of said absorbed compound as said absorbed compound travels along said wicking means and said indicating cover further including an indicator for indicating whether said tablet has melted sufficiently to indicate sterilization of said fabric pack.

* * * * *